United States Patent
Vivien et al.

(10) Patent No.: US 10,099,969 B2
(45) Date of Patent: Oct. 16, 2018

(54) PROCESS FOR THE ISOMERIZING DEHYDRATION OF A PRIMARY ALCOHOL FEEDSTOCK SUBSTITUTED IN POSITION 2 BY AN ALKYL GROUP ON A CATALYST COMPRISING AN IRON-TYPE ZEOLITE

(71) Applicants: TOTAL RESEARCH & TECHNOLOGY FELUY, Seneffe (BE); IFP Energies nouvelles, Rueil-Malmaison (FR)

(72) Inventors: Tom Vivien, Lyons (FR); Sylvie Maury, Mornant (FR); Vincent Coupard, Villeurbanne (FR); Delphine Bazer-Bachi, Irigny (FR); Nikolai Nesterenko, Nivelles (BE); Nadiya Danilina, Uccle (BE)

(73) Assignees: TOTAL RESEARCH & TECHNOLOGY FELUY, Seneffe (BE); IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 15/514,280

(22) PCT Filed: Sep. 22, 2015

(86) PCT No.: PCT/EP2015/071802
§ 371 (c)(1),
(2) Date: Mar. 24, 2017

(87) PCT Pub. No.: WO2016/046242
PCT Pub. Date: Mar. 31, 2016

(65) Prior Publication Data
US 2017/0341996 A1    Nov. 30, 2017

(30) Foreign Application Priority Data

Sep. 26, 2014 (FR) ..................................... 14 59113

(51) Int. Cl.
*C07C 1/24* (2006.01)
(52) U.S. Cl.
CPC ............ *C07C 1/24* (2013.01); *C07C 2529/65* (2013.01)

(58) Field of Classification Search
None
See application file for complete search history.

(56) References Cited

U.S. PATENT DOCUMENTS

| 9,346,773 B2 * | 5/2016 | Coupard | C07D 301/03 |
| 9,353,074 B2 * | 5/2016 | Coupard | C07D 301/03 |
| 2013/0190547 A1 | 7/2013 | Coupard et al. | |
| 2013/0204057 A1 | 8/2013 | Adam et al. | |
| 2013/0217943 A1 * | 8/2013 | Minoux | C07C 1/24 |
| | | | 585/640 |
| 2017/0355650 A1 * | 12/2017 | Minoux | C07C 1/24 |

FOREIGN PATENT DOCUMENTS

| WO | 2011/113834 A1 | 9/2011 |
| WO | 2013/011208 A1 | 1/2013 |

OTHER PUBLICATIONS

International Search Report dated Dec. 14, 2015, issued in corresponding PCT/EP2015/071802, 3 pages.
English translation Abstract of WO2013/011208A1 published Jan. 24, 2013 (1 page).
Canizares, P. et al., "Isomerization of n-butene over ferrierite zeolite modified by silicon tetrachloride treatment", Applied Catalysis A: General, vol. 190, 2000, pp. 93-105.

* cited by examiner

*Primary Examiner* — Philip Y Louie
(74) *Attorney, Agent, or Firm* — Millen, White, Zelano and Branigan, P.C.

(57) ABSTRACT

Isomerizing dehydration of feedstock containing a primary alcohol substituted in position 2 by an alkyl group in which the feedstock is heated to the reaction temperature by indirect heat exchange then vaporization by mixing with a diluent effluent, the diluted and vaporized feedstock being dehydrated in at least one dehydration reactor operating in gas phase at an inlet temperature comprised between 250 and 375° C., at a pressure comprised between 0.2 MPa and 1 MPa and at a WHSV comprised between 1 and 18 h$^{-1}$, in the presence of a catalyst comprising a zeolite having at least one series of channels the opening of which is defined by a ring with 8 oxygen atoms (8MR) and a binder, the catalyst being coked beforehand in-situ or ex-situ, so as to produce a dehydration effluent, the latter being treated and separated into a diluent effluent, an alkenes effluent and a heavy hydrocarbons effluent.

10 Claims, No Drawings

PROCESS FOR THE ISOMERIZING DEHYDRATION OF A PRIMARY ALCOHOL FEEDSTOCK SUBSTITUTED IN POSITION 2 BY AN ALKYL GROUP ON A CATALYST COMPRISING AN IRON-TYPE ZEOLITE

TECHNICAL FIELD OF THE INVENTION

The present invention relates to an improved process for the production of alkenes starting from a feedstock comprising a primary monoalcohol substituted in position 2 by an alkyl group. This feedstock can be obtained by chemical processes or by fermentation processes. This process implements a shaped catalyst based on a zeolite comprising at least one series of channels, the opening of which is defined by a ring of 8 oxygen atoms (8MR) and pre-coked.

The alkenes obtained, in particular isobutene, 1-butene and 2-butenes, are of significant interest in the field of the petrochemical industry and organic synthesis.

PRIOR ART

Isobutene is a key molecule in petrochemistry and for the synthesis of gasoline additives such as ETBE and MTBE. The great majority of publications relate to the production of isobutene starting from linear butanols, the latter being more easily produced by conventional fermentation methods (ABE) than isobutanol. However, recent developments have made it possible to greatly improve the fermentation yields of isobutanol, making this feedstock accessible and available at an attractive price.

Document WO2009/079213 describes the sequence of reactions for the dehydration of biosourced (C2-C7) alcohols on an acid catalyst in order to form olefins followed by the oligomerization of the olefins on an acid oligomerization catalyst (zeolite or alumina). The intended application is the preparation of Jet fuel.

Document EP 2348 005 describes the dehydration of alcohols containing from 2 to 10 carbon atoms to the corresponding olefin on a FER zeolite catalyst having a Si/Al atomic ratio of less than 100. The weight hourly space velocity (WHSV) with respect to the alcohol is at least 4 h$^{-1}$ and the temperature from 320 to 600° C.

Document WO 2011/089235 extends this invention to other structural types of zeolites all belonging to the family of zeolites having a medium channel size (10MR) and Si/Al molar ratio less than 100. The zeolites can be modified by different post-treatments. The inventor claims the dehydration of alcohols containing from 2 to 10 carbon atoms to the corresponding olefin.

Document WO 2011/113834 describes the simultaneous dehydration and skeletal isomerization of isobutanol in the presence of crystalline silicate catalysts having a medium channel size (10MR) dealuminated or not, phosphorus modified or not, of the FER, MWW, EUO, MFS, ZSM-48, MTT, MFI, MEL or TON group, having a Si/Al ratio greater than 10, silicoaluminophosphate molecular sieves of the AEL group, or silicated, zirconated, titanated or fluorinated alumina on zeolite catalysts. The WHSV with respect to the alcohol is at least 1 h$^{-1}$ and the temperature from 200 to 600° C. The maximum proportion of n-butenes reached in the butenes is 58.4% at 375° C. at a high WHSV (12.6 h$^{-1}$) on a FER zeolite in powder form having a Si/Al of 33. No concept of the stability of these performance levels as a function of time under load is mentioned in this document. The only other catalyst exemplified is gamma alumina.

The dehydration of $C_4$ alcohols on acid solids is generally accompanied by position isomerization of the alkene formed. These two reactions are in effect concomitant, since the position isomerization of the alkene double bond is equally as fast as the dehydration reaction of the $C_4$ monoalcohol. In the case of isobutanol, the isobutene initially formed is easily protonated (formation of a tertiary carbocation) and can then undergo secondary reactions, in particular dimerization, then cyclization, with a risk of leading to the formation of unwanted secondary products.

However, in the particular case of simultaneous dehydration and skeletal isomerization of isobutanol on non-zeolite solids, Kotsarenko et al., Kin. Katal. 24, 877 (1983) describes a mechanism in which an intermediate species of the primary carbocation type formed by dehydration on an acid site of the alcohol is rearranged via a methyl shift reaction in order to form a secondary carbocation and promote the formation of linear butenes. The catalysts with the best performance are disorganized mixed oxides based on alumina and silica, with an aluminium content of less than 5%. The maximum proportion of n-butenes reached in the butenes is 32.7% at temperatures comprised between 275 and 350° C.

Document FR2733701 describes a selectivizing pretreatment for the isomerization of linear olefins to isobutene by bringing the catalyst into contact with one or more hydrocarbon-containing molecules, therefore not comprising oxygen, containing from 4 to 10 carbon atoms, at a pressure comprised between 0.1 and 1 MPa and at a temperature comprised between 300 and 550° C. This results in an increase in selectivity to isobutene and a reduction in the conversion of the butenes. The present invention on the other hand relates to improving the selectivity to linear butenes.

In an article dealing with the isomerization of n-butene on ferrierite zeolite modified by treatment with silicone tetrachloride, Cañizares et al., Applied Catalysis A: General 190 (2000) 93-105 disclose that a high selectivity to the production of isobutene can be obtained by deposition of coke on the catalyst. Surprisingly, the utilization of the catalyst according to the invention makes it possible to obtain a greater proportion of linear butenes, and therefore a lower selectivity for isobutenes, by carrying out precoking of the catalyst.

The present invention relates to a set of operating conditions, choice of process and preparation of a zeolite catalyst making it possible, by conversion of a primary monoalcohol substituted in position 2 by an alkyl group to an alkene, to reach a proportion of linear alkenes in the alkenes fraction that is much greater than the value expected at thermodynamic equilibrium, with total conversion of the alcohol and a total alkenes selectivity greater than 97%.

OBJECT AND BENEFIT OF THE INVENTION

The invention relates to a thermally integrated process for the conversion of a feedstock comprising a primary monoalcohol substituted in position 2 by an alkyl group on a pre-coked catalyst comprising a zeolite comprising at least one series of channels, the opening of which is defined by a ring of 8 oxygen atoms (8MR) which makes it possible to produce a mixture of alkenes rich in linear alkenes.

The process according to the invention makes it possible to obtain, at the end of the reaction step, an effluent comprising a proportion of linear alkenes that is greater than that expected taking account of the thermodynamic equilibrium between the alkenes at the temperature of the outlet from the reactor, with an excellent conversion and a very good selectivity.

The process according to the invention also makes it possible to limit the thermal degradation of the feedstock by implementing suitable heating, as well as an overall reduction in the quantity of hot and cold utilities required.

DETAILED DESCRIPTION OF THE INVENTION

The invention relates to a process for the isomerizing dehydration of a feedstock comprising from 40 to 100% by weight of primary alcohol substituted in position 2 by an alkyl group comprising at least the following steps:
a) Pressurization of said feedstock then preheating the compressed feedstock by heat exchange with the dehydration effluent originating from step c) in a heat exchanger so as to produce a preheated feedstock;
b) Vaporization of said feedstock preheated by mixing with the diluent effluent originating from step f), the ratio of the diluent effluent mass flow rate to the preheated feedstock being comprised between 5/95 and 60/40;
c) Dehydration of the effluent originating from step b) in at least one dehydration reactor operating in gas phase at a weighted average temperature comprised between 250 and 375° C., at a pressure comprised between 0.2 MPa and 1 MPa and at a WHSV comprised between 1 and 18 $h^{-1}$, in the presence of a catalyst comprising a zeolite having at least one series of channels the opening of which is defined by a ring with 8 oxygen atoms (8MR), said catalyst being coked beforehand in-situ or ex-situ, so as to produce a dehydration effluent;
d) Cooling of said dehydration effluent by at least three successive indirect heat exchanges with at least one water effluent originating from step e), then said compressed feedstock from step a), then a cold utility so as to produce a cooled effluent;
e) Settling of said cooled effluent into an aqueous phase and an organic phase, one part of said aqueous phase being purged in order to be treated outside of said dehydration process and the other part, forming the water effluent, being recycled via step f);
f) Recycling of the water effluent originating from step e) and at least partial vaporization by heat exchange in a heat exchanger with the dehydration effluent originating from step c), separation of any liquid fraction that may be present, then compression and superheating of the vapour fraction in order to form a diluent effluent, said diluent effluent being recycled to step b);
g) Separation of the organic phase extracted from step e) in at least one distillation column so as to produce an alkene effluent and a heavy hydrocarbons effluent.

Feedstock

According to the invention, the feedstock treated in the process according to the invention is a feedstock comprising from 40 to 100% by weight of at least one primary monoalcohol substituted in position 2 by an alkyl group. Said monoalcohol is preferentially isobutanol or 2-methyl-1-butanol, used alone or in a mixture, and very preferentially isobutanol. In the remainder of the disclosure, by the term "primary alcohol" is meant the primary monoalcohol. By the term "alkyl" is meant a hydrocarbon-containing compound of general formula $C_nH_{2n+1}$ in which n is an integer comprised between 1 and 20, preferably between 1 and 10, preferably between 1 and 5.

Said feedstock can originate from chemical or biochemical processes, for example fermentation processes. In particular, this feedstock can originate from lignocellosic biomass fermentation processes.

Said feedstock also advantageously comprises from 0 to 60% by weight of water. Said feedstock can also comprise impurities of the mineral type (such as Na, Ca, P, Al, Si, K, $SO_4$), and organic type (such as methanol, ethanol, n-butanol, aldehydes, ketones and the corresponding acids, for example furanic, acetic, isobutyric acid).

Preheating Step a)

According to the invention, said feedstock comprising a primary monoalcohol substituted in position 2 by an alkyl group is pressurized in a pump then preheated by heat exchange with the dehydration effluent originating from step c) in at least one heat exchanger so as to produce a preheated feedstock.

Said pump makes it possible to increase the pressure of said feedstock to a pressure comprised between 2 and 10 bar. The heat exchange makes it possible for the feedstock to be heated to a temperature comprised between 100 and 250° C., preferentially between 100 and 150° C.

Vaporization Step b)

According to the invention, the preheated feedstock originating from step a) is vaporized by mixing with the diluent effluent originating from step f).

The diluent effluent originating from step f) is constituted by water and impurities dissolved up to the extent of their solubility under the conditions of the settling step e). This effluent is vaporized, compressed, superheated in step d) so as to provide sufficient energy for the vaporization of the diluent effluent mixture and preheated feedstock. The temperature of the effluent after its superheating is comprised between 400 and 650° C., preferentially between 425 and 550° C.

The ratio of the diluent effluent mass flow rates to the preheated feedstock is comprised between 5/95 and 60/40.

The preheated feedstock/diluent effluent mixture is then taken to a temperature comprised between 250° C. and 375° C. in an oven.

When envisaging a temperature of the heated fluid at the outlet of the heating equipment, for example an oven, the temperature of the exchange surface is often much higher than the envisaged temperature, the difference possibly being of the order of 100° C. On contact with the walls, the heated fluid is thus subjected to high temperatures. Therefore, if 250 to 375° C. is envisaged at the outlet of the oven, the heated mixture is exposed on contact with the walls to temperatures of the order of 350 to 475° C. Heating the feedstock in three steps comprising a first step of heating by heat exchange in a heat exchanger followed by a second step of heating by mixing with the hot diluent effluent and a third step of heating in an oven makes it possible to avoid the primary monoalcohol substituted in position 2 by an alkyl group experiencing concentrated exposure, i.e. in a mixture comprising more than 95% by weight of primary monoalcohol substituted in position 2 by an alkyl group, to temperatures greater than 280° C. The primary monoalcohol substituted in position 2 by an alkyl group is thus protected against the risks of thermal degradation, which improves the overall yield of the process.

Dehydration Step c)

According to the invention, the effluent originating from step b) then supplies a dehydration step.

The dehydration step comprises at least one dehydration reactor. When this step comprises more than one reactor, the temperature at the inlet of each of the reactors is adjusted to a value comprised between 250 and 375° C. by a heating means, as the isomerizing dehydration reaction is endothermic, and each reactor is operated under identical conditions. Thus, in the remainder of the disclosure, the term "the reactor" denotes both the reactor of said step c), when the latter comprises only one reactor, and each of the reactors of said step c), when the latter comprises more than one reactor.

The reactor is operated in gas phase, at a weighted average temperature comprised between 250 and 375° C., at a pressure comprised between 0.2 MPa and 1 MPa and at a WHSV comprised between 1 and 18 h$^{-1}$, in the presence of a catalyst comprising a zeolite comprising at least one series of channels the opening of which is defined by a ring with 8 oxygen atoms (8MR). Said catalyst is placed in one or more fixed beds, which can be operated under ascending, descending or radial flow.

By WHSV is meant "Weight Hourly Space Velocity", i.e. the mass flow rate of primary alcohol substituted in position 2 by an alkyl group in the feedstock at the inlet of the reactor divided by the mass of catalyst in said reactor.

By weighted average temperature is meant the average of the temperature in the catalytic bed calculated along the axis of flow in said bed. Given a bed of length L and surface area S with the reaction mixture flowing along the longitudinal axis x of this bed, the inlet to the catalytic bed forming the origin of the axis (x=0), the weighted average temperature is expressed according to:

$$WAT = \frac{1}{L}\int_0^L T(x)dx$$

According to the invention, said catalyst is pre-coked in situ or ex situ with a feedstock comprising a primary alcohol substituted in position 2 by an alkyl group at a partial pressure in said primary alcohol strictly greater than that of the feedstock of the process, or with said pure primary alcohol. By said pure primary alcohol is meant that said primary alcohol substituted in position 2 by an alkyl group comprises less than 1% by weight of compounds other than said primary alcohol, preferably less than 1000 ppm, preferably less than 100 ppm, very preferentially less than 10 ppm and very preferably that it does not comprise other detectable compounds. In another arrangement, the pre-coking could be carried out with the heavy hydrocarbons effluent originating from separation step g).

In a first embodiment of the invention, the pre-coking is carried out at a weighted average temperature strictly greater than the operating temperature of the reaction and comprised between 250 and 450° C., advantageously between 300 and 450° C., and very advantageously between 400 and 450° C., a pressure comprised between 0.1 and 3 MPa, advantageously between 0.1 and 0.5 MPa, and a WHSV comprised between 0.1 et 10 h$^{-1}$, advantageously between 0.1 and 3 h$^{-1}$.

In a second embodiment of the invention, the pre-coking is carried out at a weighted average temperature strictly less than the weighted average operating temperature of the reaction and comprised between 200 and 350° C., preferentially between 225 and 325° C., a pressure strictly greater than the operating pressure of the reaction and comprised between 0.1 and 3 MPa, advantageously between 1.1 and 3 MPa, preferentially comprised between 1.2 and 3 MPa, and a WHSV comprised between 0.1 et 10 h$^{-1}$, preferentially between 0.1 and 3 h$^{-1}$. This embodiment makes it possible in particular to avoid the deposition of heavy coke on the catalyst.

In these two embodiments, the pre-coking is carried out for a duration of 1 to 30 h, preferably from 2 to 24 h. This pre-coking, carried out either at a weighted average temperature strictly greater than the weighted average temperature of operation of the isomerizing dehydration reaction, or at a weighted average temperature strictly less and a pressure strictly greater than the weighted average temperature and operating pressure of the isomerizing dehydration reaction makes it possible to significantly improve the selectivity of the catalyst to linear alkenes, beyond that expected if the thermodynamic equilibrium between the alkenes at the outlet temperature of the oven is considered. It is carried out prior to the implementation of said catalyst in order to produce the isomerizing dehydration reaction of the feedstock comprising primary alcohol substituted in position 2 by an alkyl group.

The conversion drops regularly during the operation. The catalyst is regularly regenerated by combustion of the coke in the presence of oxygen diluted in nitrogen, the dilution being adjusted so as to maintain a temperature within the catalytic bed comprised between 400 and 600° C. This regeneration is followed by a pre-coking according to the invention before the catalyst is returned to operation.

The duration of pre-coking is considered as sufficient if, during the operation of the reactor so as to carry out the isomerizing dehydration reaction of said process feedstock, the $C_5^+$ selectivity is less than 1% for a conversion of said primary monoalcohol substituted in position 2 by an alkyl group comprised in said process feedstock greater than 97%. The $C_5^+$ selectivity is defined as the ratio of the difference between the mass flow rate of carbon element comprised in the hydrocarbons having at least 5 carbon atoms in the dehydration effluent and the mass flow rate of carbon element comprised in the hydrocarbons having at least 5 carbon atoms in the effluent originating from step b), to the difference between the mass flow rate of carbon element comprised in the primary alcohol substituted in position 2 by an alkyl group comprised in the effluent originating from step b) and the mass flow rate of carbon element comprised in the primary alcohol substituted in position 2 by an alkyl group comprised in the dehydration effluent.

According to the invention, the catalyst utilized in step c) comprises a zeolite having at least one series of channels, the opening of which is defined by a ring of 8 oxygen atoms (8MR) as defined in the classification "Atlas of Zeolite Structure Types", C. Baerlocher, L. B. McCusker, D. H. Olson, 6th Edition, Elsevier, 2007, Elsevier".

According to a particular embodiment, the zeolite can also advantageously contain at least a series of channels, the pore opening of which is defined by a ring containing 10 oxygen atoms (10MR).

Said zeolite is advantageously selected from the zeolites of structural type FER and MFS, and more advantageously from the ferrierite, FU-9, ISI-6, NU-23, ZSM-35 and ZSM-57 zeolites, used alone or in a mixture. Said zeolite is very advantageously ferrierite.

Said catalyst comprises said zeolite shaped in a matrix constituted by an inert binder. In fact, said zeolite cannot be used industrially in powder form. The binder makes it possible to give the final sold increased strength in the presence of water.

The mass ratio of the binder to said zeolite of said catalyst is comprised between 50/50 and 10/90.

Very advantageously, said catalyst is constituted by ferrierite zeolite and silica binder.

Said catalyst used in the process according to the invention is advantageously prepared according to a preparation process comprising at least the following steps:
1) a step of mixing at least one zeolite powder in protonic or ammonium form with at least one powder of at least one binder, for example an amorphous silica powder, which contributes to controlling the porosity of the final solid, and at least one solvent in the presence of a peptizing agent;
2) a step of adding a solvent, advantageously water, so as to modulate the loss on ignition of the paste and to obtain the desired textural properties for the final solid;
3) a step of forming the pasty mixture obtained at the end of stage 2) for example by extrusion,
4) a step of drying the shaped material obtained at the end of step 3), advantageously at a temperature comprised between 50 and 200° C., preferentially between 80 and 150° C., advantageously for a duration comprised between 1 and 24 h, and advantageously under air;
5) an optional step of calcinating at a temperature ranging from 400 to 800° C. for a period ranging from 2 to 12 h;
6) an optional step of heat treatment, such as oven drying at a temperature comprised between 500-700° C. under moist air, i.e. comprising from 6 to 50% by volume of water in the air.

The binder used in step 1 may be selected from the binders well known to a person skilled in the art, and more particularly from those that are "inert" with respect to the operating conditions and in particular the presence of water in the process. Thus, a silicic binder, an aluminophosphate binder or a clay may advantageously be used.

A source of silicic binder can be a precipitation silica or a silica originating from by-products such as fly ash, for example the silica-alumina or silica-calcium particles, and fumed silica. Advantageously, a colloidal silica may be used, in the form for example of a stabilized suspension, such as for example commercial products such as Ludox® or Klebosol®.

The amorphous silica powder advantageously used in step 1) of the process for the preparation of the catalyst used according to the invention preferably has a granulometry adapted to 1.4 or 1.8 μm.

The powders are advantageously mixed in the presence of a solvent (step 2), preferably water, in which a peptizing agent can advantageously be dissolved in order to obtain a better dispersion of the binder. The consistency of the paste is adjusted by means of the quantity of solvent.

The peptizing agent used during this step can advantageously be an acid, an organic or inorganic base such as acetic acid, hydrochloric acid, sulphuric acid, formic acid, citric acid and nitric acid, alone or in a mixture, soda, potash, ammonium hydroxide, an amine, a quaternary ammonium compound, selected from the alkyl-ethanol amines or the ethoxylated alkyl-amines, tetraethylammonium hydroxide and tetraethylammonium.

The protocol for shaping the solid must not modify the access to the active part thereof: the zeolite, and must facilitate the diffusion of the reagents in the solid. The shaped catalyst can adopt any shape known to a person skilled in the art, such as tablet, granule, mono- or polylobed extrudate, sphere.

Said catalyst is micro/meso/macroporous.

Cooling Step d)

The effluent originating from the last reactor in step c) is at a temperature of approximately 250° C., in vapour phase.

According to the invention, the effluent from step c) is cooled by at least three successive heat exchanges, with at least the water effluent originating from step e), then said compressed feedstock from step a), then a cold utility so as to produce a cooled effluent. The heat exchanges are carried out in heat exchangers the technology of which is well known to a person skilled in the art (plate heat exchangers, shell and tube heat exchangers, or other suitable systems).

The effluent from step c) is cooled and partially condensed at the outlet of the first heat exchange with the water effluent originating from step e). The cooling is continued with the second heat exchange with the pressurized feedstock from step a), then with the third exchange with the cold utility. At the end of the third heat exchange, the effluent from step c) is totally condensed, and at a temperature of less than 50° C. It is then conveyed to settling step e).

The heat exchanges are carried out in heat exchangers known to a person skilled in the art, which may comprise several shells and, optionally, a by-pass circuit by-passing one or more of these shells in order to regulate the temperature of the outlet flows. The cold utility can be air, cooling water, and/or any other available fluid allowing the effluent originating from step c) to reach a temperature of less than 50° C.

Settling Step e)

According to the invention, the effluent from step c), cooled and condensed in step d), supplies a settling step e). A demixing takes place and settling step e) makes it possible to separate an aqueous phase and an organic phase.

The aqueous phase comprises more than 90% by weight of water, preferentially greater than 95% by weight of water. The water content of the aqueous phase depends greatly on the presence of species that do not react in dehydration step c) and are soluble in water, which are all found in said aqueous phase, such as for example methanol, ethanol, acetaldehyde, acetone and the corresponding acids. It also comprises compounds present in the organic phase, as a function of their solubility, mainly a few ppm of oxygenated compounds and approximately 5 ppm of primary alcohol substituted in position 2 by an alkyl group.

The organic phase contains primary alcohol substituted in position 2 by an alkyl group that has not reacted, as well as alkenes and the heavy products produced during dehydration step c).

The aqueous phase is drawn off with a view to recycling. A part of this phase is purged so as to maintain the content of heavy compounds in the recycling at a value of a few ppm. This purged part can be treated outside the process. The non-purged part, which forms the water effluent, is recycled by means of recycling step f). The organic phase is treated in separation step g) in order to produce at least one alkenes effluent.

The purged fraction represents from 0 to 30% of the extracted aqueous phase, advantageously from 5 to 20% of this phase.

Recycling Step f)

The water effluent drawn off in settling step e) is depressurized. By depressurized is meant that its pressure is reduced. The depressurization determines the low pressure point of the water recycling loop.

The depressurized water effluent is reheated by heat exchange in a heat exchanger with the effluent from dehydration step c), during which it is at least partially vaporized. By partially vaporized is meant that at least 90% by weight of the depressurized effluent is vaporized.

The depressurization of the water effluent is adjusted so as to recover the maximum heat during the heat exchange with the effluent from step c), i.e. the vaporization at the outlet of the heat exchanger is at least 90% by weight of the water effluent, but without being total.

The liquid fraction optionally present is separated in a separator drum intended to protect the compressor from any presence of liquid (called a K.O. Drum). The vapour fraction, separated from the liquid fraction, is compressed in a compressor. The depressurization fixes the high pressure point of the recycling loop.

The adjustment of the high pressure point and the low pressure point of the process makes it possible on the one hand to ensure sufficient pressure in dehydration step c), but also to ensure maximum recovery of the heat from the dehydration effluent by vaporizing at least 90% of the water effluent. This adjustment is also carried out in such a way that, while recovering the maximum heat from the dehydration effluent, the temperature of the vapour fraction of the water effluent is such that at the end of the compression, the temperature does not exceed 300° C. so as not to damage the equipment.

The compressed vapour fraction, at a temperature that does not exceed 300° C., is superheated in a heat exchanger, for example an oven at a temperature comprised between 400° C. and 650° C.

In a preferred arrangement, a single oven is used for heating the preheated feedstock/diluent effluent mixture during step b) and for superheating the compressed vapour fraction, the latter being superheated in the hot part of the oven, while said mixture is brought to temperature in the cold part.

The compressed and superheated vapour fraction forms the diluent effluent. This effluent is then mixed with the preheated feedstock originating from step a) in order to ensure its evaporation.

Separation Step g)

According to the invention, the organic phase extracted from step e) is treated in a separation step so as to produce an alkenes effluent and a heavy hydrocarbons effluent.

Said separation step comprises at least one distillation column. Said organic phase is separated by distillation and at the top a distillate is recovered comprising the alkenes and at the bottom a residue comprising the heavy products as well as the primary alcohol substituted in position 2 by an alkyl group that has not reacted.

This column has from 5 to 20 theoretical plates, advantageously from 5 to 15. The column is operated at a pressure comprised between 0.5 and 1 MPa, with a temperature at the top comprised between 50 and 90° C. and a temperature at the bottom comprised between 100 and 150° C.

The distillate is advantageously conveyed to a drier that is necessary to adjust the water content depending on the downstream applications.

The primary alcohol substituted in position 2 by an unconverted alkyl group, comprised in the residue, can advantageously be recycled in a mixture with the feedstock of the process according to the invention.

EXAMPLES

Example 1 (not According to the Invention): Heating of Isobutanol

This example shows the thermal decomposition of pure isobutanol when it is taken to a high temperature.

Pure isobutanol, i.e. in particular free of water, is vaporized in an oven in which a bed of inert carborundum (SiC) has been installed in order to promote heat exchange. It is exposed to several temperatures, at a pressure of 0.1 MPa. The WHSV is 1 h$^{-1}$. The effluent composition is analyzed. The results are shown in Table 1.

1.5% of the isobutanol is converted at 300° C. to products of the dehydrogenation, dehydration and isomerization of isobutene, and other unidentified products. 4.5% of the isobutanol is converted at 400° C.

TABLE 1

Analysis of the effluent at the outlet of the heating zone

| molar % | feedstock | 300° C. | 350° C. | 400° C. | 450° C. |
|---|---|---|---|---|---|
| Isobutanol | 99.35 | 98.93 | 98.99 | 95.51 | 86.22 |
| 2-butanone | 0.55 | 0.61 | 0.29 | 0.42 | 0.45 |
| 1-butanol | 0.07 | 0.07 | 0.07 | 0.06 | 0.05 |
| 2-butanol | | 0.02 | 0.02 | 0.09 | 0.13 |
| Isobutyraldehyde | | 0.1-0.31 | 0.43 | 2.59 | 8.24 |
| Isobutene + 1-butene | | 0.04 | 0.18 | 1.05 | 3.39 |
| 2-butenes | | | 0.02 | 0.12 | 0.42 |
| propane | 0.01 | 0.01 | | 0.07 | 0.6 |
| methane | | | | 0.02 | 0.14 |

The ratio of surface area $A(H_2)/A(N_2)$ and the ratio $H_2$ at outlet/iC$_4$OH at inlet make it possible to demonstrate the occurrence of the dehydrogenation reaction and the impact of the temperature on the latter.

Description of the Catalytic Test Unit and of the Catalysts Used for Examples 2 to 5

Examples 2 to 5 are carried out on a test unit comprising a fixed bed operating in downflow mode, i.e. descending flow. The catalyst is loaded in the form of extrudates of 3 mm in length in a 316L stainless steel reactor having an internal diameter of 13 mm. The catalyst is then activated at 450° C. under 6 l/h of air during a plateau of one hour, after a temperature increase of 10° C./min, the temperature is then reduced to the test temperature under 6 l/h of nitrogen in order to eliminate the air present in the system before injection of the feedstock.

The feedstock is vaporized in the lines heated to 150-180° C. upstream of the reactor then injected into the catalytic reactor. Each temperature and WHSV condition is maintained for a minimum of 24 h (the minimum duration of a test is 96 h). The catalyst is regenerated several times under air at 500° C.

The catalyst A is prepared by co-mixing 80% of ferrierite having a Si/Al atomic ratio of 20 and 20% of silicic binder. The solid was extruded, dried at 80° C. for 12 h, then calcined under dry air for 2 h at 600° C. The catalyst A obtained has a SBET specific surface of 321 m$^2$/g, a mesoporous volume of 0.11 cc/g, a macroporous volume of 0.35 cc/g and a microporous volume of 0.11 cc/g.

Example 2

Dehydration of an isobutanol/water feedstock in a mass ratio of 95/5 of catalyst A to catalyst B. this example shows the benefit of pre-coking.

The catalyst B is prepared by co-mixing 80% of ferrierite having a Si/Al atomic ratio of 10 and 20% of silicic binder. The solid was extruded, dried at 80° C. for 12 h, then calcined under dry air for 2 h at 600° C. The catalyst B obtained has a SBET specific surface of 320 m$^2$/g, a mesoporous volume of 0.09 cc/g, a macroporous volume of 0.19 cc/g and a microporous volume of 0.11 cc/g.

Firstly, the catalysts were tested without pre-coking at 0.2 MPa, WHSV 3 h$^{-1}$, and a weighted average temperature (WAT) of 350° C.

The same catalysts were pre-coked beforehand under a feedstock of isobutanol+water at 1.2 MPa, WAT of 350° C. WHSV 3 h$^{-1}$ for 6 h then tested at 0.2 MPa, WHSV 3 h$^{-1}$, WAT of 350° C. The catalytic performance of the catalysts, pre-coked or not, were measured. The results are given for the two catalysts A and B, pre-coked or not, in the table below. The data below were obtained after 6 h under load. By $C_3^+$ is meant propene, by $C_4^+$ is meant butenes, and by $C_5^+$ is meant hydrocarbons having at least 5 carbon atoms.

| Description | | Isobutene selectivity (%) | Yield of linear butenes (% wt)* | C3+ salt (%) | C5+ salt (%) | C4+ salt (%) | Isobutanol conversion (%) | % linear butenes in the C4 olefins |
|---|---|---|---|---|---|---|---|---|
| Catalyst A | Not pre-coked | 24.5 | 72.4 | 0.05 | 2.4 | 96.9 | 100.0 | 74.7 |
|  | pre-coked | 18.7 | 80.6 | 0.0 | 0.4 | 99.5 | 99.9 | 81.2 |
| Catalyst B | Not pre-coked | 24.9 | 50.1 | 2.03 | 19.7 | 75 | 100 | 50.1 |
|  | pre-coked | 18.2 | 80.5 | 0.05 | 1.0 | 98 | 99.7 | 80.4 |

*calculation performed on a carbon base, without taking account of the water fraction eliminated On a loaded pre-coked catalyst, the conversion of alcohol remains total, the total butenes selectivity increases as a result of a significant drop in the selectivity for $C_5^+$ et $C_3^+$ products for which it is normally accepted that these originate from the dimerization-cracking of butenes to propylene plus $C_5$. Thus, for a zeolite, whatever its starting Si/Al and its initial selectivity, pre-coking under selected conditions makes it possible to obtain a catalyst that is much more selective for the conversion of isobutanol into linear butenes by limiting the formation of products heavier than $C_4$. This makes it possible to bring the selectivity of a catalyst that was initially not very selective to that of a more selective catalyst.

Example 3

Dehydration of an isobutanol/water feedstock in a mass ratio of 95/5 on catalyst A. this example shows that ferrierite catalyzes a reaction in which the linear olefins are a primary product of the reaction.

The operating conditions and the catalytic results are given below. The reactor is maintained at an operating pressure of 0.2 MPa. The catalyst is not pre-coked. The data are obtained by averaging the values over 24 h.

| T (° C.) | WHSV (h$^{-1}$) | Isobutene salt (%) | C5+ salt (%) | C4+ salt (%) | Alcohol conversion (%) | linear butenes in the C4 olefins (%) |
|---|---|---|---|---|---|---|
| 300 | 21 | 23.65 | 2.2 | 97.4 | 99.1 | 75.7 |
| 300 | 12 | 24.16 | 2.4 | 97.3 | 99.8 | 75.2 |
| 300 | 5 | 25.24 | 2.6 | 97.0 | 100.0 | 74.0 |
| 300 | 3 | 27.43 | 3.2 | 96.3 | 100.0 | 71.5 |
| 300 | 1 | 32.34 | 5.0 | 94.1 | 100.0 | 65.6 |

* the other secondary products making it possible to round the sum of the selectivities to 100% are mainly isobutyraldehyde, isobutane and propane/propylene.

An increase in the WHSV leads to a reduction in the selectivity for isobutene and an increase in the selectivity for linear butenes. This indicates that isobutene is not a primary product of the reaction, which would undergo a skeletal isomerization in order to form linear butenes. On the other hand, it is the linear olefins that are the primary products of the reaction. The catalyst according to the invention makes it possible to obtain a proportion of linear butenes in the total butenes that is considerably greater than the value expected at thermodynamic equilibrium which is comprised between 45 and 55%, as well as a selectivity for butenes that is greater than 96% except for the WHSV of 1 h$^{-1}$. The dehydration of isobutanol is total, regardless of the operating conditions, except for the highest WHSV.

Example 4

Dehydration of a 1-butanol/water feedstock in a mass ratio of 95/5 and an isobutanol/water feedstock in a mass ratio of 95/5 on catalyst A. this example shows that the catalyst according to the invention does not promote the skeletal isomerization of linear butenes.

A test was carried out using a 1-butanol feedstock diluted with 5% water or with an isobutanol feedstock diluted with 5% water that has been reacted in the presence of catalyst A under an operating pressure of 0.2 MPa.

Catalyst A is pre-coked with the feedstock at 1.2 MPa, 350° C., WHSV 3 h$^{-1}$ for 6 h. It is thus used according to the invention.

| WAT (° C.) | WHSV (h$^{-1}$) | Isobutene salt (%) | C5+ salt (%) | C4+ salt (%) | Alcohol conversion (%) | % linear butenes in the C4 olefins |
|---|---|---|---|---|---|---|
| Butanol/water feedstock 1 | | | | | | |
| 350 | 6 | 12.6 | 2.6 | 97.0 | 99.9 | 84.1 |
| 375 | 6 | 15.6 | 2.2 | 97.3 | 100.0 | 81.7 |
| 375 | 12 | 10.3 | 1.9 | 97.9 | 99.9 | 87.6 |
| 350 | 3 | 7.9 | 1.2 | 98.6 | 100.0 | 90.6 |
| Isobutanol/water feedstock | | | | | | |
| 350 | 6 | 19.8 | 0.6 | 99.1 | 99.1 | 80.1 |
| 375 | 6 | 20.9 | 0.4 | 99.4 | 99.5 | 78.9 |
| 375 | 12 | 20.4 | 0.3 | 99.5 | 99.0 | 79.5 |
| 350 | 3 | 18.7 | 0.4 | 99.5 | 99.7 | 81.2 |

It will be noted that the test at 350° C. and WHSV 6 with an isobutanol/water feedstock on the catalyst used according to the invention can be compared to Example 1 of WO 2011/113834, second column. In fact, the WHSV in this document is calculated on the weight of ferrierite. In the table herein, the WHSV is calculated on the basis of the catalyst, which contains 20% binder and 80% ferrierite. Consequently, a WHSV of 6 corresponds to a WHSV according to WO 2011/113834 of 6/0.8=7.5. A better selectivity for $C_4^+$ and a proportion of linear butenes in the $C_4$ olefins is noted that is much greater with the catalyst utilized according to the invention.

The catalyst utilized according to the invention makes it possible to obtain a proportion of linear butenes in the total butenes that is considerably greater than the value expected at thermodynamic equilibrium which is comprised between 45 and 55%, as well as a selectivity for butenes that is greater than 97%. The dehydration of isobutanol is total, regardless of the operating conditions. The selectivity for linear butenes is almost identical whether starting from the butanol or the isobutanol feedstock. The catalyst does not promote the skeletal isomerization of the linear butenes in isobutene, even by extending the contact time (by lowering the WHSV). This indicates that the catalyst utilized according to the invention based on ferrierite has a particular selectivity for promoting the formation of linear butenes and not of isobutene starting from isobutanol or 1-butanol under the operating conditions selected.

Example 5 (Comparative)

This example shows the benefit of zeolites of FER structural type having channels 8 and 10MR over zeolites of the TON and MTT structural type having only 10MR channels.

Four zeolites containing 10MR channels of the FER structural type (8-10MR two-dimensional ferrierite), TON (10MR one-dimensional NU-10) and MTT (10MR one-dimensional ZSM-23) were compared. These zeolites were tested in powder form having a granulometry of 400-500 μm at WAT of 350° C. and at WHSV 3 h$^{-1}$, 0.2 MPa.

The catalysts are pre-coked with the feedstock at 1.2 MPa, 350° C., WHSV 3 h$^{-1}$ for 6 h. Catalysts A and B are thus used according to the invention.

| Catalyst ref. | WHSV (h$^{-1}$) | C3+ salt (%) | C5+ salt (%) | C4+ salt (%) | Isobutanol conversion (%) | % linear butenes in the C4 olefins |
|---|---|---|---|---|---|---|
| B | 3 | 0.05 | 1.0 | 98 | 99.7 | 80.4 |
| A | 3 | 0.0 | 0.4 | 99.5 | 99.9 | 81.2 |
| Nu-10 Si/Al 30 | 3 | 1.1 | 14.8 | 82.7 | 100.0 | 57.8 |
| ZSM-23 Si/Al 22 | 3 | 8.2 | 59.5 | 16.5 | 99.3 | 44.5 |

Only the ferrierites make it possible to reach proportions of linear butenes in the olefins C4 cut that are greater than the composition at thermodynamic equilibrium as well as a high selectivity for butenes. With all the zeolites, the alcohol conversion is total. The ZSM-23 zeolites on the other hand have a very degraded selectivity and promote the formation of C5+ et de C3+. The zeolite Nu-10 is slightly more selective but promotes even more strongly the formation of secondary products.

Example 6

Dehydration of an isobutanol/water feedstock in a mass ratio of 95/5 on catalyst A. this example shows that the ferrierite catalyzes a reaction in which the linear olefins are a primary product of the reaction. this example, compared with Example 3, shows the beneficial effects of the pre-coking according to the invention at a low temperature.

The operating conditions and the catalytic results are given below. The reactor is maintained at an operating pressure of 0.2 MPa. Le catalyst is pre-coked. The data are obtained by averaging the values over 24 h.

| T (° C.) | WHSV (h$^{-1}$) | Isobutene salt (%) | C5+ salt (%) | C4+ salt (%) | Alcohol conversion (%) | linear butenes in the C4 olefins (%) |
|---|---|---|---|---|---|---|
| 300 | 21 | 22.51 | 0.2 | 99.7 | 99.0 | 85.1 |
| 300 | 12 | 23.04 | 0.3 | 99.6 | 99.5 | 85.0 |
| 300 | 5 | 24.12 | 0.4 | 99.5 | 99.6 | 84.6 |
| 300 | 3 | 26.31 | 0.4 | 99.5 | 99.8 | 84.5 |
| 300 | 1 | 30.14 | 0.6 | 98.9 | 100.0 | 82.8 |

* the other secondary products making it possible to round the sum of the selectivities to 100% are mainly isobutyraldehyde, isobutane and propane/propylene.

As in Example 3, an increase in the WHSV results in a reduction in the selectivity for isobutene and an increase in the selectivity for linear butenes. This indicates that isobutene is not a primary product of the reaction, which would undergo a skeletal isomerization in order to form linear butenes. The catalyst according to the invention makes it possible to obtain a proportion of linear butenes in the total butenes that is considerably greater than the value expected at thermodynamic equilibrium which is comprised between 45 and 55%, as well as a selectivity for butenes that is greater than 99% except for the WHSV of 1 h$^{-1}$. The dehydration of isobutanol is total, regardless of the operating conditions, except for the highest WHSV.

Compared with Example 3, a significant improvement in the overall selectivity for C4+ olefins produced in relation to pre-coking is noted. There is also a smaller gain in the degree of isomerization (reduction in residual isobutene), at the cost of a slight loss of activity.

The invention claimed is:

1. A process for isomerizing dehydration of a feedstock comprising from 40 to 100% by weight of primary alcohol substituted in position 2 by an alkyl group, said process comprising at least:
    a) compressing said feedstock then preheating the compressed feedstock by heat exchange with dehydration effluent originating from c) in a heat exchanger so as to produce a preheated feedstock;
    b) vaporizing said preheated feedstock by mixing with diluent effluent originating from f), at a ratio of diluent effluent mass flow rate to preheated feedstock of 5/95 to 60/40;
    c) dehydrating the vaporized feedstock from b) in at least one dehydration reactor operating in gas phase at a weighted average temperature of 250 to 375° C., at a pressure of 0.2 MPa to 1 MPa and at a WHSV of 1 to 18 h$^{-1}$, in the presence of a catalyst comprising a zeolite having at least one series of channels with openings defined by a ring with 8 oxygen atoms (8MR), wherein said catalyst is pre-coked in-situ or ex-situ, to produce a dehydration effluent;
    d) cooling said dehydration effluent in at least three successive heat exchanges with at least water effluent originating from e), then said compressed feedstock from a), and then a cold utility to produce a cooled effluent;
    e) settling said cooled effluent into an aqueous phase and an organic phase, purging a part of said aqueous phase in order to be treated outside of said dehydration process, and forming a water effluent to be recycled via step f) from another part of said aqueous phase;
    f) recycling the water effluent originating from e) and at least partially vaporizing said water effluent by heat exchange in a heat exchanger with the dehydration effluent originating from c), separating any liquid fraction that may be present, then compressing and superheating the vapor fraction to form a diluent effluent, and recycling said diluent effluent to b); and g) separating organic phase extracted from e) in at least one distillation column to produce an alkenes effluent and a heavy hydrocarbons effluent.

2. The process according to claim 1, said catalyst from c) is pre-coked with a primary alcohol substituted in position 2 by an alkyl group at a partial pressure of said primary alcohol greater than that of the feedstock, at a weighted average temperature greater than the operating temperature and of 250 to 450° C., a pressure of 0.1 to 3 MPa, a WHSV of 0.1 to 10 h$^{-1}$ and a duration of 1 to 30 h.

3. The process according to claim 1, in which said catalyst from c) is pre-coked with a primary alcohol substituted in position 2 by an alkyl group having a partial pressure of said primary alcohol greater than that of the feedstock, at a weighted average temperature less than the operating temperature and of 200 to 350° C., a pressure greater than the operating pressure of 0.1 to 3 MPa, a WHSV of 0.1 to 10 h$^{-1}$ and a duration of 1 to 30 h.

4. The process according to claim 1, in which said catalyst from c) is pre-coked with a pure primary alcohol substituted in position 2 by an alkyl group at a weighted average temperature greater than the operating temperature and of 250 to 450° C., a pressure of 0.1 to 3 MPa, a WHSV of 0.1 to 10 h$^{-1}$ and a duration of 1 to 30 h.

5. The process according to claim 1 in which said catalyst from c) is pre-coked with a pure primary alcohol substituted in position 2 by an alkyl group, at a weighted average temperature less than the operating temperature and of 200 to 350° C., a pressure greater than the operating pressure and of 0.1 to 3 MPa, a WHSV of 0.1 to 10 h$^{-1}$ and a duration of 1 to 30 h.

6. The process according to claim 1, in which said catalyst from c) is pre-coked with the heavy hydrocarbons effluent originating from separation g), at a weighted average temperature greater than the operating temperature and of 250 to 450° C., a pressure of 0.1 to 3 MPa, a WHSV of 0.1 to 10 h$^{-1}$ and a duration of 1 to 30 h.

7. The process according to claim 1, in which said catalyst from c) is pre-coked with the heavy hydrocarbons effluent originating from separation g), at a weighted average temperature less than the operating temperature and of 200 to 350° C., a pressure greater than the operating pressure and of 0.1 to 3 MPa, a WHSV of 0.1 to 10 h$^{-1}$ and a duration of 1 to 30 h.

8. The process according to claim 1, in which said zeolite in the catalyst utilized in c) is a zeolite of FER and MFS structure used alone or in a mixture.

9. The process according to claim 1, in which said zeolite in the catalyst utilized in c) is ferrierite, NU-23, FU-9, ISI-6, ZSM-35 or ZSM-57 zeolite, used alone or in a mixture.

10. The process according to claim 1, in which a single oven is used for heating the preheated feedstock/diluent effluent mixture during b) and for the superheating of the compressed vapor fraction, the latter being superheated in a hot part of the oven, while said mixture is brought to temperature in a cold part.

\* \* \* \* \*